(12) United States Patent
Junker et al.

(10) Patent No.: US 6,216,526 B1
(45) Date of Patent: Apr. 17, 2001

(54) GAS SAMPLER FOR MOLTEN METAL AND METHOD

(75) Inventors: Thomas W Junker, Oconomowoc, WI (US); Richard A Falk, Hillsboro Beach, FL (US)

(73) Assignee: Midwest Instrument Co., Inc., Hartland, WI (US)

( * ) Notice: Subject to any disclaimer, the term of this patent is extended or adjusted under 35 U.S.C. 154(b) by 0 days.

(21) Appl. No.: 09/212,916

(22) Filed: Dec. 16, 1998

(51) Int. Cl.[7] .............................. G01N 1/10; G01N 33/20
(52) U.S. Cl. ........................................ 73/19.07; 73/DIG. 9
(58) Field of Search ................. 73/19.07, DIG. 9

(56) References Cited

U.S. PATENT DOCUMENTS

| | | | |
|---|---|---|---|
| 2,861,450 | 11/1958 | Ransley | 73/19.07 |
| 3,820,380 | * 6/1974 | Miller et al. | 73/19.07 X |
| 4,170,139 | 10/1979 | Narita et al. | |
| 4,454,748 | 6/1984 | Terai et al. | 73/19.07 |
| 4,624,128 | 11/1986 | Pelton | |
| 4,731,732 | 3/1988 | Warchol et al. | 73/19.01 |
| 4,757,707 | 7/1988 | Harvey et al. | |
| 4,879,005 | 11/1989 | Fray et al. | |
| 4,918,974 | 4/1990 | Hachey et al. | |
| 4,998,432 | 3/1991 | Plessers et al. | 73/19.07 |
| 5,591,894 | * 1/1997 | Falk et al. | 73/19.07 |

* cited by examiner

Primary Examiner—Daniel S. Larkin
(74) Attorney, Agent, or Firm—Ryan Kromholz & Manion S.C.

(57) ABSTRACT

An immersion probe for determination of the concentration of a gas dissolved in molten metal includes a gas and molten metal-permeable, disk. A gas analysis method using the probe entails introducing into said metal through the probe inert gas streams which may contain a concentration of hydrogen, oxygen or nitrogen gas which is greater or less than that contained in the molten metal. The dissolved concentrations of the two gases after passage through the metal are compared and enable accurate computation of the content of hydrogen gas dissolved in the metal. Using a mass spectrometer with argon as an inert carrier, hydrogen, oxygen, and nitrogen concentrations may be determined by a single test procedure.

20 Claims, 6 Drawing Sheets

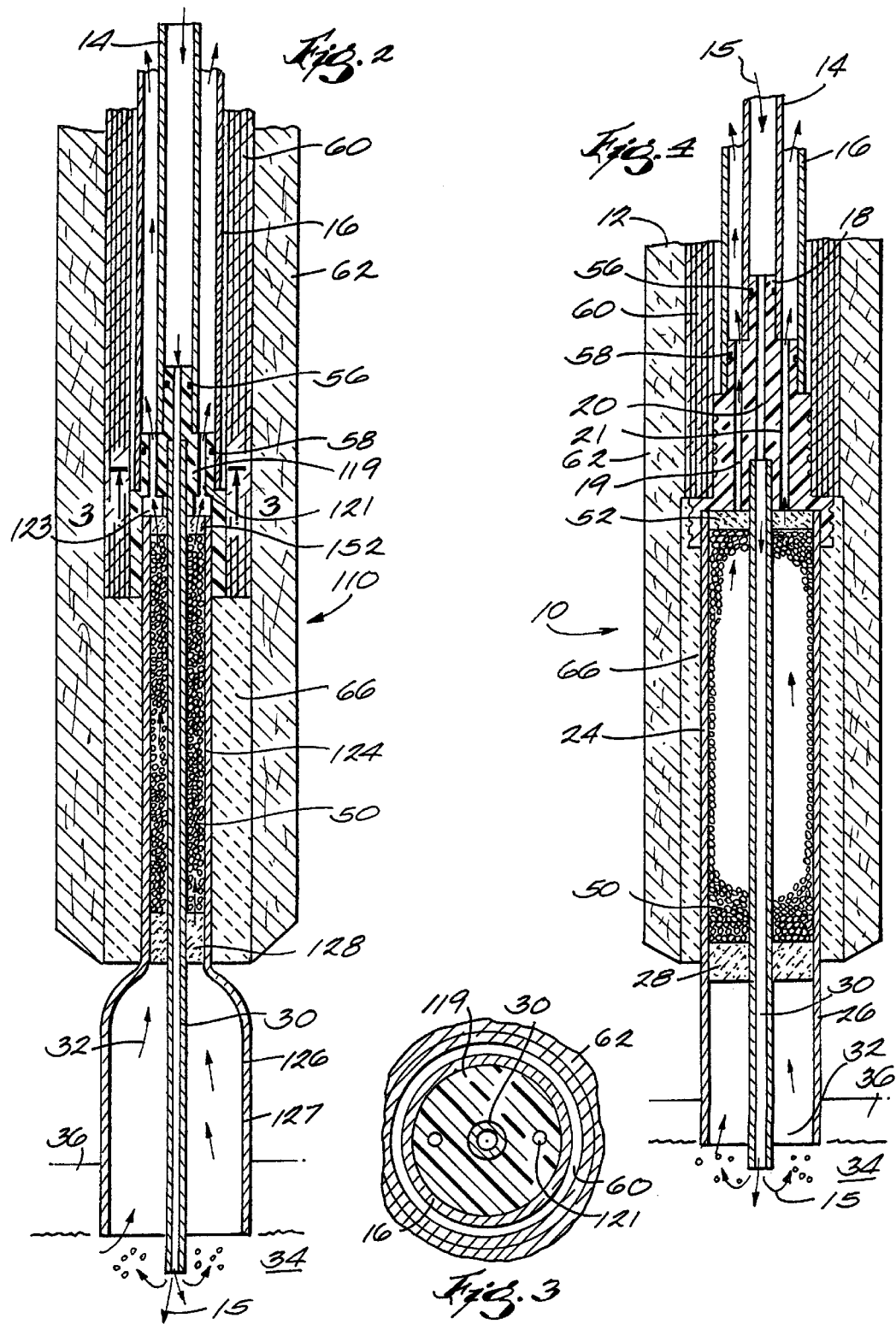

GAS SAMPLER FOR MOLTEN METAL AND METHOD

FIELD OF THE INVENTION

The invention relates to a probe for use in apparatus and a method for measurement of gas concentrations in molten metal. More particularly, the invention relates to such a probe suitable for determination of dissolved hydrogen, oxygen, and/or nitrogen content in molten metals, such as steel.

BACKGROUND OF THE INVENTION

Various devices have been developed heretofore to measure the content of dissolved gases such as hydrogen in molten metals, such as molten aluminum or molten steel. An early device is described in U.S. Pat. No. 2,861,450 issued to Ransley et al. The device shown therein is referred to as the Telegas device. This device is included in an immersion head of generally a bell-shaped configuration and entails discharging or debouching a carrier gas into the molten metal and recapturing bubbles by the probe head. These devices entailed the recirculation of the gases through a closed loop until equilibrium is reached. The nitrogen reached an equilibrium with the dissolved hydrogen, which thus enables monitoring and measurement of the dissolved hydrogen content in the metal. These devices, as well as subsequent variations thereof, uses a membrane which is permeable to the gas, usually hydrogen, whose concentration is to be determined, but which is stated to be impermeable to molten metal. A need continues to exist for such probes which offer testing of increased speed and accuracy.

SUMMARY OF THE INVENTION

It is a principal object of the invention to provide a new and improved probe and processes for determination of dissolved gas contents in molten metals. The invention has important application to the determination of the concentrations of hydrogen, oxygen, and nitrogen dissolved in molten steel, but can be used also to determine concentrations of other dissolved gases in molten steel and in other molten metals. The invention, thus, has applicability to determination of dissolved gas concentrations in most other molten metals such as copper, aluminum, tin, or lead. The invention provides such devices and methods which enable simultaneous determination of the concentration of several gases by means of a single test procedure. In a preferred embodiment using a mass spectrometer, the dissolved gases are absolutely characterized by their molecular weights, as well.

An important aspect of the invention relates to providing of an immersion probe which eliminates the use of and need for a membrane which is impermeable to molten metal. A related aspect entails use of a porous material which, instead of being impermeable to molten metal, is of a type used as a strainer for removing solid impurities from a molten metal. The new probes, by eliminating the impermeable member and substituting a porous metal-permeable material enables more rapid determinations of gas contents than heretofore possible, and, the simultaneous determination by means of a single test procedure of the concentration of a number of gases including hydrogen, oxygen, and nitrogen.

Another aspect of the invention relates to the introduction of streams of inert gases which contain known concentrations of the gas or gases being measured, at least one of these gas streams having a known concentration higher than that of the gas in the metal being tested and another one of the gas streams having a concentration less than that of the gas in the metal being tested. The true amount of the gas being characterized in the metal is then computed to a high degree of accuracy.

Briefly, the invention provides an immersion probe for determination of the concentration of a gas dissolved in molten metal which includes a probe body in the form of an elongated housing. The probe body is formed of a gas and molten metal impervious material of sufficient thermal resistance to withstand immersion in molten metal for the analysis time and is connected to a gas conduit for inflow of an inert gas. The immersible end of the probe body has a porous member which, unlike previous devices, may be, in a preferred embodiment, permeable to both gas and liquid molten metal. The porous member is loosely fitted and unsealed in the probe head and serves to support a layer of loose insulation material, and acts as a heat and splash shield.

An inert carrier gas, such as nitrogen or argon, is used in practice of the process of this invention. After immersion, the probe of this embodiment is preferably purged with pure inert dry gas having a known concentration of hydrogen gas for about fifteen-thirty seconds, and then a negative pressure is drawn through a thermal conductivity device (TCD) such as a katharometer using a pump, a step which is continuous and reaches equilibrium within less than about forty-five seconds. Dissolved gas concentration is then rapidly determined by a connected analysis device.

The method for determining gas contents in molten metal in accordance with the invention includes the steps of providing a probe as defined above, the probe being connected by a gas flow conduit to a gas analysis device. The probe is immersed in the molten metal and then preferably purged and standardized with a pure inert carrier gas stream until an equilibrium is reached and recorded. Then, in accord with a preferred procedure, a stream of pure carrier gas is introduced through the probe which contains predetermined known concentrations of gases to be analyzed, usually hydrogen, oxygen, and/or nitrogen gas which are greater than those contained in the molten metal until equilibrium is recorded. The gases are recovered by the submerged hollow or bell-shaped submerged probe end as it bubbles through the metal bath. The analysis device is then used to determine the content of hydrogen, oxygen, and/or nitrogen contained in the gas flowing out of the metal. Subsequently, there is introduced into the molten metal, through the probe, a second gas stream of an inert carrier gas which contain second predetermined concentrations of hydrogen, oxygen, and/or nitrogen gas which are less than those contained in the molten metal. The second gas is also recovered and analyzed as it bubbles out of the metal to determine its content of hydrogen, oxygen, and/or nitrogen. The gas content determinations are then compared and used to accurately and absolutely compute the content of gases dissolved in the metal. If a mass analyzer, such as a quadrupole mass gas analyzer, is used as the gas analysis device, determinations of hydrogen, oxygen, and nitrogen contents may be effected with high accuracy using a single test procedure.

Other aspects and advantages of the invention will be apparent from the following detailed description, claims, and accompanying drawings.

BRIEF DESCRIPTION OF THE DRAWINGS

FIG. 2 is a central cross sectional view of a preferred form of probe for use in connection with the invention;

FIG. 3 is a fragmentary sectional view taken along Line 3—3 of FIG. 2;

FIG. 4 is a central cross sectional view showing an alternative embodiment of a probe of the present invention;

DETAILED DESCRIPTION OF THE INVENTION

Figure 1:
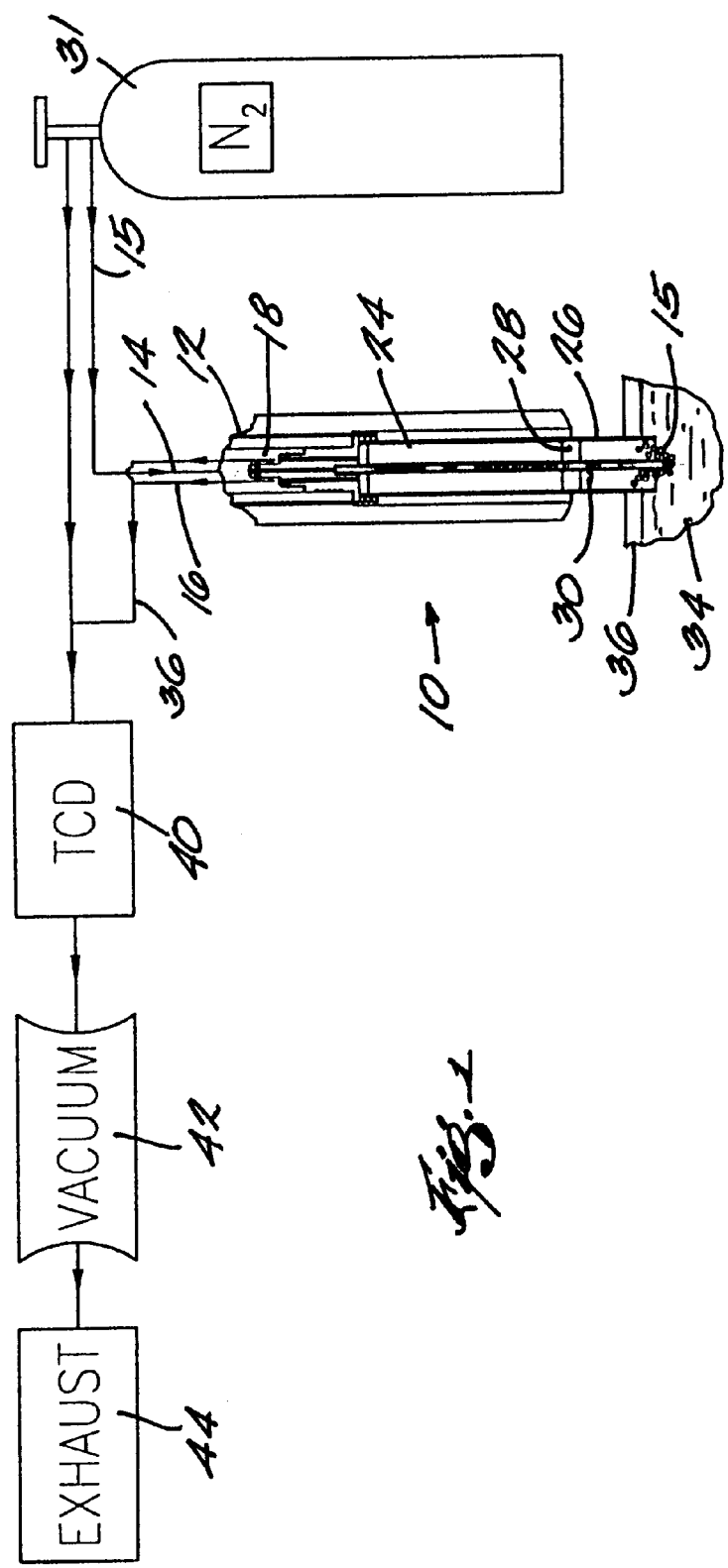
FIG. 1 is a schematic diagram illustrating the practice of the invention including a probe, shown in cross section, together with a fragmentary view of a molten metal bath.

Referring more particularly to the drawings, there is seen in FIG. 1 a schematic view illustrating the practice of the invention. In FIG. 1, probe 10 is immersible into a molten metal bath 34 to determine the content of gases dissolved therein. In accordance with the preferred embodiment of the invention, the content of hydrogen dissolved in a molten iron or steel bath is determined. Probe 10 includes an upper end 12 adapted to be supported on a steel pole and to be connected by conduits to a source of inert gas as well as to instrumentation (not shown) by means of appropriate connections. An inlet tube 14 which conducts a stream 15 of inert gas, such as nitrogen or argon, connects to a central internal nipple component 18 of a metal fitting 19, as shown in figure four. An outflow line 16 is provided to direct the flow of gas emerging from the probe to an analysis device. Probe 10 is seen in greater detail in FIG. 4.

Probe 10 includes a tubular body portion 24, preferably formed of quartz. Tubular portion 24 has an open lower end 26 adapted to be immersed in molten metal 34 which is contained in a suitable containment vessel 36. As the stream 15 of inert gas emerges from the bottom end of tube 30, an equilibrium amount of the hydrogen contained in bath 34 is mixed with stream 15, the bubbles emerging from bath 34 being captured by the lower end 26 of the probe 10, as illustrated by arrows 32. Unlike previous probes, probe 10 includes a disk 28 which is preferably molten metal permeable. Disk 28 is preferably loose fitting and serves as a splash protector while also supporting a free-flowing particulate insulation 50.

As seen in FIG. 1, the stream of gas 32 containing hydrogen recovered as it diffuses from the molten metal 34 is drawn by vacuum into a thermal conductivity device 40 identified in the schematic drawing by its initials "TCD". One example of such a device is a katharometer-based system, such as the Alscan analyzer available from Bomem Inc. of Quebec, Canada. Since such devices are known in the art and do not constitute a novel part of the present invention, they are thus not described in detail herein.

Also, it will be noted that by eliminating the use of a gas recirculating loop, heretofore a standard part of hydrogen detection probes used in molten metals, a vacuum pump 42 can be used to facilitate rapid flow of the stream of gas 32 through the thermal conductivity device 40 to increase the speed of the analysis procedure. After a stream of gases 32 flows through the thermal conductivity device, the stream is exhausted harmlessly into the atmosphere through an exhaust port 44. In the drawings, the source of dry inert gas 31 is identified as being nitrogen gas. However, those skilled in the art will recognize that other inert gases, for example argon, can be substituted.

The thermal conductivity device may be, for example, a katharometer such as is described in "Gas Analysis by Measurement of Thermal Conductivity" H. A. Daynes, Cambridge University of Press, 1933. Other devices which may be substituted include gas chromatographs, thermal conductivity cells, or mass spectrometers.

Reference is again made to FIG. 4 relating to the details of the probe 10. Filter element 28 is preferably a porous alumina disk of a type generally used to filter impurities from molten metal. The use of the very porous and loose-fitting metal molten metal permeable disk 28 enables freer flow and greater flow rates through the system of the carrier gases and more rapid recovery and analysis of the gas content of the metal. Higher speed determinations of the dissolved gas contents in the molten metal are thus facilitated. The interior of tubular body 24 is preferably filled with a loose inert particulate filler 50. Filler 50 may be either in the form of solid or hollow particles generally in the size range of 5–200 $\mu$m in average diameter. Disk 28 serves to confine the filler 50 at the lower end thereof. A particulate filler 50 is confined at the upper end of the probe by another disk 52 which may simply be a layer of an inert material, such as ceramic "wool" fibers.

Filler 50 may be in the form of hollow ceramic spheres such as those sold under the trade name Duralum AB bubbles, available from Washington Mills Electrominerals Corporation of Niagara Falls, New York. Solid heat resistant inorganic particles may be used, instead, if desired.

As seen in FIG. 4, connector block fitting 19 is provided with an inner bore 20 which conducts the inflowing inert gas 15 from inflow port 14 into glass tube 30. An O-ring connector 56 provides a leak proof seal between tube 14 and nipple end 18 of connector block fitting 19. If desired, the tube 14 can be provided with a mating metal or plastic end (not shown) to connect to and fit tightly over nipple end 18. Similarly, outer passageways 21, which are spaced apart from bore 20, accommodate the flow of gas for testing out from the probe body 24 into outflow tube 16 which is concentric with inflow tube 14. Another O-ring 58 provides a leak proof connection between fitting 19 and outflow tube 16. Again, a fitting (not shown) may be integral with the end of outflow tube 16 and adapted to fit tightly over the shoulder of fitting 19 which supports O-ring 58.

The probe device 10 is supported on a cardboard tube 60 in conventional fashion. Cardboard tube 60 may be of any desired length, but typically will be of a length of approximately thirty four inches in order to facilitate support and handling of the probe 10 during immersion into bath 34. A layer of ceramic fiber 62 preferably surrounds the body of probe 10 as shown. Ceramic fiber layer 62 is a high temperature resistant material which may be formed by drawing a fiber-colloidal ammonium silicate mixture under a vacuum. A layer of potting cement 66 may be used to bind together the parts of probe 10 as shown. In particular the potting cement 66 hardens to form a body supporting lower end of fitting 19 and glass tube 24 against the lower end of cardboard tube 60 to form an integral probe body.

Referring to FIG. 2, there is seen a modified version 110 of a probe of this invention. In the probe 110 of FIG. 2, parts which are numbered the same as in FIG. 2 refer to the same components. As seen, a modified connector block fitting 119 is provided with modified flow openings 121 which have an enlarged lower end 123. An end view of the connector block fitting 119 is seen in FIG. 3. In the modification of FIG. 2, the collecting tube 124 has a lower end 126 formed of a bell-shaped configuration 127. The enlarged bell shaped portion 127 facilitates the collection of the stream of collected gas 32 which bubbles out of the molten metal bath 34.

A metal and gas permeable disk 128 is modified in shape in order to fit between the interior of tube 124 and the exterior of the inner glass tube 30. A porous disk 152 is also provided at the upper end of an appropriate shape to fit the upper end of glass tube 124.

Figure 5:
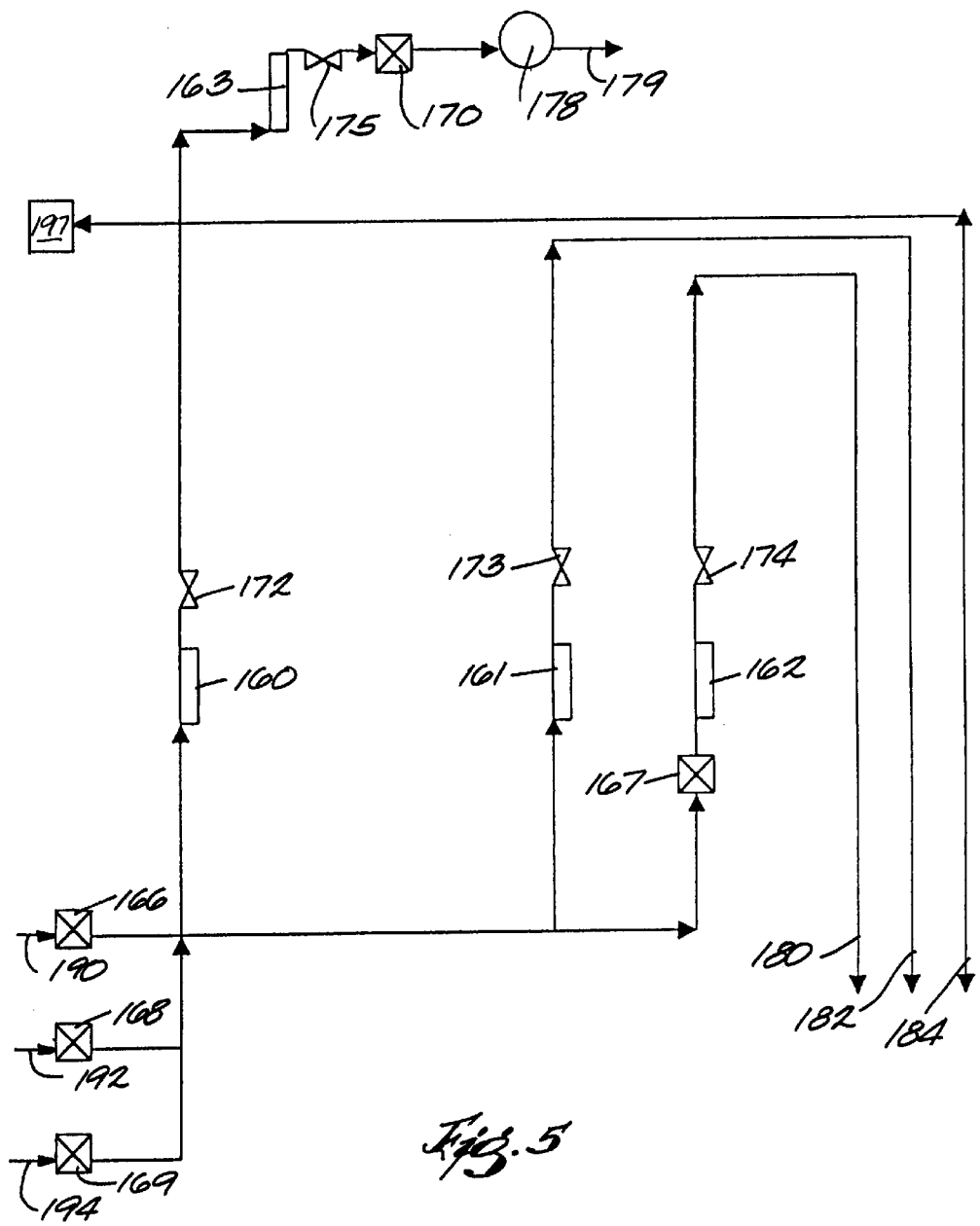
FIG. 5 is a flow diagram showing a preferred arrangement for practice of the invention using a mass spectrometer.

In FIG. 5, there is seen a flow diagram illustrating the relationship between the components of a preferred system used in the practice of the invention. In FIG. 5, rectangles 160, 161, 162, and 163 indicate flow meters provided within the system. Valves 166, 167, 168, 169, and 170 are solenoid activated valves used to control the flow of gases through the system. Valves 172, 173, 174, and 175 are metering valves. A vacuum pump 178 which exhausts to the atmosphere through a conduit 179 is provided to induce desirably rapid flow rates of gases through the system. Solenoid valves 166, 168, and 169 serve to control input of gases into the system. One line 190 is provided to supply pure inert carrier gas, such as nitrogen or argon. Another input line 192 controlled by solenoid valve 168 provides a supply of a carrier gas having a predetermined content of a gas, such as hydrogen or oxygen, to be determined mixed in the carrier gas. A further input conduit 194 controlled by solenoid valve 169 supplies containing a different concentration of gas, such as hydrogen or oxygen, which is to be tested for. Line 196 is an intake line to a mass spectrometer 197 used to determine the concentration of gases in the molten metal being tested. A katharometer device such as an Alscan TCD, may be used in addition to or instead of the mass spectrometer. Using Sievert's Law, the percent of a dissolved gas in the molten metal is derived from the partial pressure of that gas in the single line system at equilibrium.

Line 180 is a purge line used only during a purge cycle. Line 182 represents a constant purging line which may be open both during the purge cycle and the analysis cycle. Line 184 is a purge and intake line which purges during the purge cycle and serves to draw gases into the mass spectrometer 197 or other TCD, such as a katharometer, if used, during the analysis cycle. The preferred mass spectrometer includes its own turbomolecular pump to draw in a sample, in addition to pump 178, whereas in the case of a katharometer, the pump 178 is needed to draw gases into the TCD.

When hydrogen is tested for, for example, a loss of hydrogen from the carrier gas to the molten steel takes place when the hydrogen content in the supplied carrier gas is higher than the hydrogen in the steel. A hydrogen content reading from higher hydrogen containing carrier gas has been found to be 0.3 to 0.4 ppm higher than a hydrogen reading using pure inert carrier gas. Hydrogen readings from carrier gases containing hydrogen mixtures lower than the hydrogen content in steel will read the same as or 0.1 to 0.2 ppm higher than a pure carrier gas. A processor is preferably used to compute the gas content in the metal based on comparison of the values obtained by a test using an elevated hydrogen and the value obtained by a test using a reduced hydrogen content. The later may either be zero or a preselected amount below the estimated content in the metal. The processor includes an output terminal to output the computed dissolved gas content.

The preferred system shown in the drawings system incorporates a non-recirculating single line gas analysis system to continuously supply fresh carrier gas to the system, bubble fresh carrier gas through the sensor, into the molten metal, collect the carrier gas containing the collected gases and dissolved gas such as hydrogen from the molten metal, and drawing the gases from the immersed sensor through the TCD instrument with vacuum, after which the gases are exhausted into the atmosphere. The single line from the carrier gas source to the atmospheric exhaust is broken only by the bubbling of the gas through the molten metal and the collection of the gases. This takes place in steel at the lower end of the sensor which is immersed from six to nine inches into the steel melt. This open exhaust single line system allows the quick removal of impurities that might be drawn into the system prior to the analysis or which exist, if any, in the expendable immersion probe or generated during the initial immersion and purge of the system. Impurities, for example, could result from the burning away of a paper slag cap, if used, the melting of the sensor's metal inner cap, or random minor impurities that may have been introduced into the sensor during the sensor manufacture, or, for example, water vapor remaining in the sensor as manufactured. These are purged through the system and completely exhausted from the system usually within eighteen to twenty seconds during the pre-analysis immersion into the melt during the purge cycle and the initial part of the analysis cycle.

The system of this invention also does not require a device which signals that the probe is immersed into the steel, as seen in the prior art. An economical nitrogen inert carrier gas can flow continuously for short periods of time before the start of the purge cycle and after the completion of the analysis cycle in applications where nitrogen content is not being measured.

The timing sequences of a typical reading are as follows:
1. Push Start: Zero seconds;
2. Purge out of the molten metal: Fifteen to twenty five seconds;
3. Purge in the molten metal: ten to twenty seconds;
4. Zero setting: five seconds with pure nitrogen or argon;
5. Reading the equilibrium of the carrier and its unknown gas content: thirty to ninety seconds.

Sequence two allows time for the operator to get into position for immersion and allows the system to fully purge itself before immersion with the inert carrier gas. Sequence three is used to remove any impurities as discussed above from the sensor sampling chamber and to prevent and counteract the pressure of the molten metal from filling up the sampling chamber during immersion. Sequence four allows the TCD to memorize the base line zero reading of the inert gas carrier and establish a new zero point for each individual reading. Sequence five involves drawing unknown gases collected in up to three different carrier gases from the sensor through the detector and exhaust to the atmosphere using an aspirated vacuum or vacuum pump until an equilibrium measure is reached and read. The initial satisfactory equilibrium is reached between thirty five and sixty seconds, and sequential initial equilibria are reached in approximately, twenty seconds for each.

Figure 6:
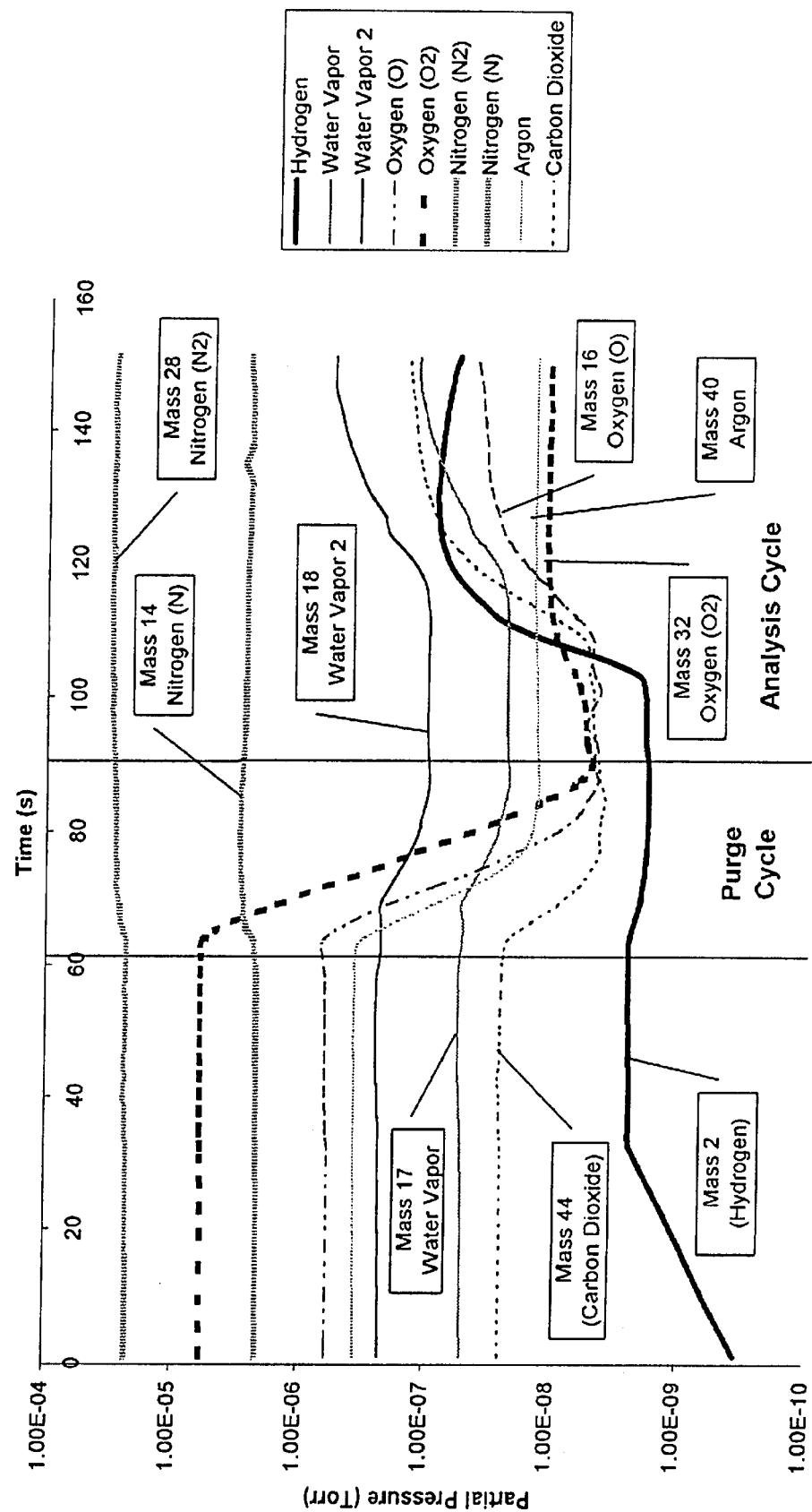
FIG. 6 is a typical print-out of an analysis of dissolved gases in molten steel using a mass spectrometer.
Figure 7:
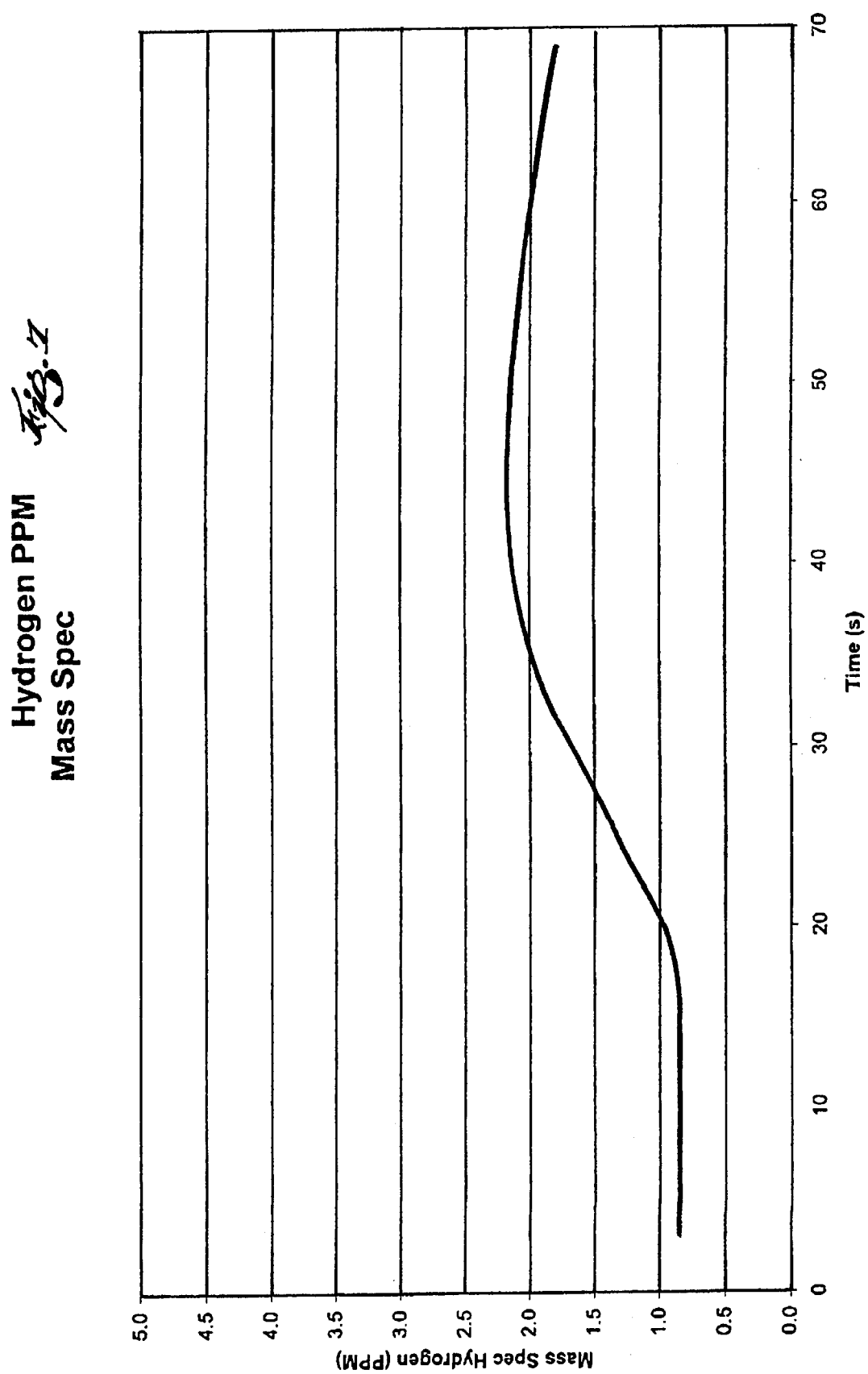
FIG. 7 is a typical print-out of an analysis of dissolved hydrogen content in molten steel using a mass spectrometer; and, FIG. 8 is a print-out of the analysis of dissolved hydrogen content in the same batch of molten steel as shown in FIG. 7, but obtained using an Alscan TCD (katharometer).
Figure 8:
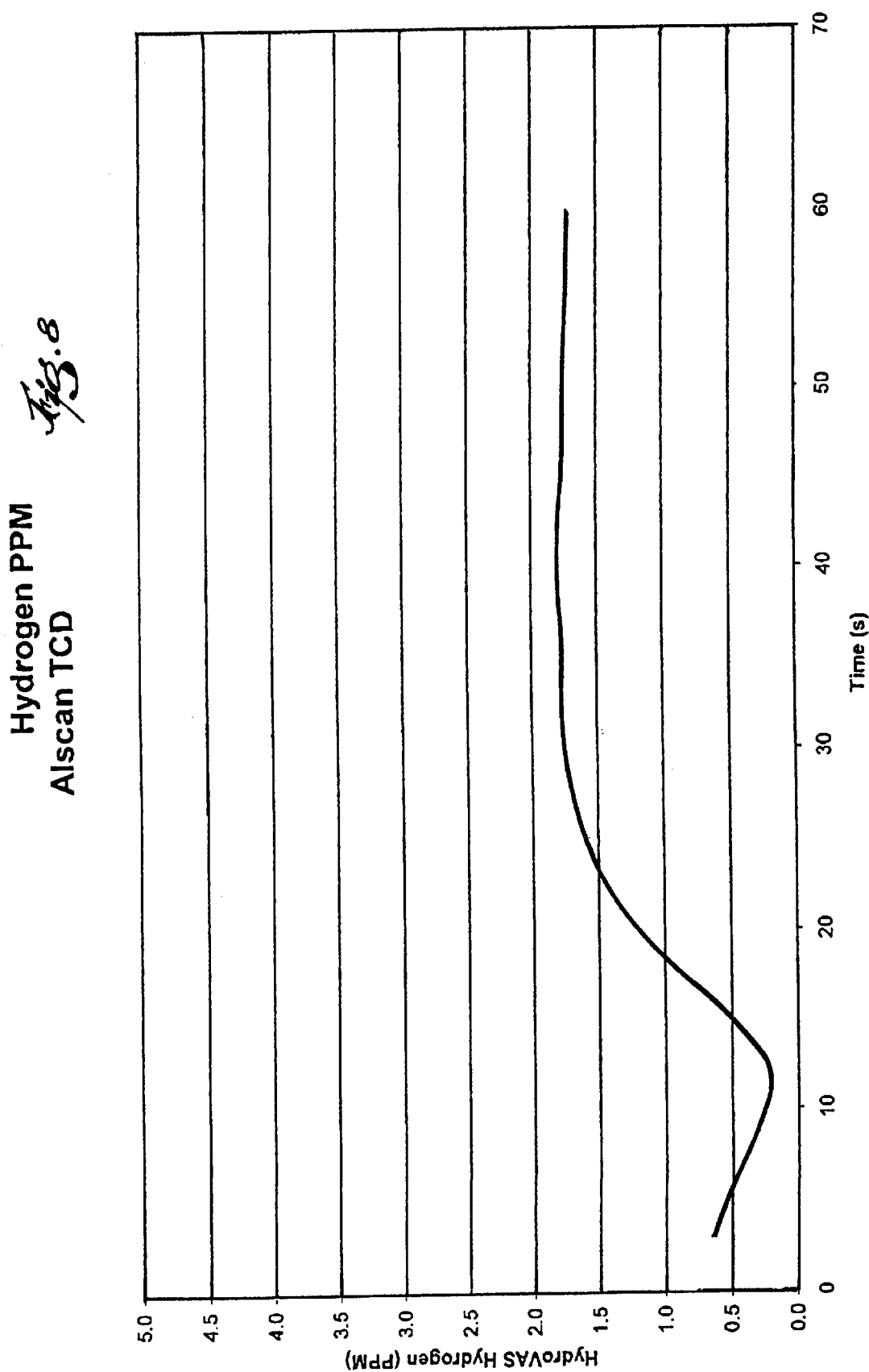

A preferred detection device for use with the sensor system of this invention is the PPT series of residual gas analyzers manufactured by NGS, a division of MKS Instruments, Inc., 24 Walpole Park South, Walpole, Mass. The instrument is a semi-portable, compact, computerized, low molecular weight mass spectrograph which operates under extremely high vacuums. The mass spectrograph characterizes analytically any gas collected by a carrier gas having a molecular weight less than two hundred with a potential sensitivity of one part per one hundred million. The mass spectrograph obtains a micro sample of gas from the gases being drawn from the immersion sensor device through the vacuum system and purged to the atmosphere, and within thirty seconds to one minute identifies and displays the analytical gases collected. An example Mass spectrograph display curve is shown in FIG. 6 wherein partial pressure traces are labeled by molecular weight. For example, hydrogen is one and two, oxygen is sixteen and thirty two, each curve being thus identified by the molecular weight of the detected gas.

Calibrations have been obtained to convert, by means of a microprocessor, partial pressures of the detected gases from the mass spectrometer display into part per million of hydrogen, oxygen, and nitrogen. For example, calibrations made to relate the partial pressure (in Torr) to the calculated hydrogen content (in ppm) in steel was accomplished by measuring high purity precisely standardized hydrogen/nitrogen mixtures from 1.5 ppm $H_2$ to 19.89 using an Alscan katharometer instrument simultaneously with the mass spectrometer and the comparative results plotted on an x/y scatter plot and a best-fit trend line. This type of comparison study can also be used to accurately calibrate other gases of interest, such as $O_2$ and $N_2$, to the partial pressure readout of the mass spectrometer.

The Alscan instrument and the MKS Mass Spectrograph can be used simultaneously during the same steel plant production analysis cycle. One verifies the absolute accuracy and precision of the other's reading.

The MKS instrument is also able to determine oxygen in steel simultaneously with hydrogen in steel when using nitrogen carrier gas. The MKS Mass Spectrograph is also able to determine nitrogen, hydrogen, and oxygen in steel in ppm's precisely, accurately, and simultaneously using a different carrier gas, such as argon.

The qualitative and quantitative accurate simultaneous analyses of three different gases, hydrogen, nitrogen, and oxygen in steel using a mass spectrograph attached to a probe directly immersed in molten steel is a significant advance in the art. This procedure is applicable in ingot, production ladles, and continuous casting process equipment to levels lower than one ppm, by the mass spectrographic method with excellent precision and accuracy in less than two minutes, a total process time and accuracy heretofore unknown and unaccomplished in the trade.

While various preferred embodiments of the invention have been shown for purposes of illustration it will be understood that the invention is not be limited thereto, but includes equivalent structures falling within the true scope of the appended claims.

What is claimed is:

1. An immersion probe for determination of the concentration of a gas dissolved in molten metal by immersion of said probe in said metal comprising:
   a probe body in the form of a housing having an elongated configuration, said body being formed of a gas and molten metal impervious material of sufficient resistance to withstand immersion in molten metal;
   said body having a first end provided with a fluid flow inlet adapted to be connected to a gas inflow conduit and a fluid flow outlet adapted to be connected to a gas analysis device;
   said body having a second end adapted to be immersed in molten metal, said second end being spaced away from said first end and having a first fluid flow opening in fluid flow communication with said fluid flow inlet for discharge of gas into said molten metal, and a second fluid flow opening for recovery of gas from said molten metal, said second opening being in gas and liquid metal fluid flow communication with said fluid flow outlet, and being gas and liquid metal permeable.

2. A probe according to claim 1 wherein said second end of said probe body is provided with a gas and molten metal permeable disk which forms a molten metal splash-preventing member partly closing said second end but allowing flow through said second end of molten metal and gases.

3. A probe according to claim 2 wherein said disk comprises a porous refractory material.

4. A probe according to claim 3 wherein said disk comprises alumina.

5. A probe according to claim 1 wherein said elongated body comprises a quartz tube.

6. A probe according to claim 5 adapted to measure gas content within a selected metal and wherein the exterior of said quartz tube is surfaced by a layer of said selected metal.

7. A probe according to claim 1 wherein said inlet comprises a centrally positioned gas flow opening.

8. A probe according to claim 7 wherein a connector block is attached to said first end, said inlet extending centrally through said block and at least one outflow opening radially displaced from said inlet also extends through said block.

9. A probe according to claim 8 in which said connector block is hermetically sealed to the upper end of said probe body.

10. A probe according to claim 1 wherein said outlet of said first end of said probe is connected to a gas analysis device.

11. A probe according to claim 1 wherein a portion of said elongated body between the first and second ends is provided with a protective layer of heat resistant material.

12. A probe according to claim 10 wherein said gas analysis device is a mass spectrometer.

13. A method for determining content of gases in molten metal comprising:
   providing a molten metal immersible probe which is connected by a gas flow conduit to a gas analysis device;
   immersing said probe in said molten metal;
   introducing into said metal through said probe a stream of an inert carrier gas which contains a first known concentration of a gas to be detected, which is greater than the concentration of that gas contained in the molten metal;
   recovering said carrier gas as said carrier gas bubbles out of said metal and using said analysis device to determine the content of said gas contained in the gas flowing out of said metal;
   introducing into said metal through said probe a second inert carrier gas which contains a second known concentration of said gas less than that contained in the molten metal;
   recovering said second inert gas as said second inert gas bubbles out of said metal and using said analysis device to determine the content of said gas contained in the gas flowing out of said metal; and,
   comparing said gas content determinations to compute the content of said gas dissolved in said metal.

14. A method according to claim 13 wherein said inert carrier gas comprises nitrogen or argon.

15. A method according to claim 13 wherein said analysis device is a thermal conductivity device.

16. A method according to claim 13 wherein said analysis device is a katharometer.

17. A method according to claim 13 wherein said analysis device is a mass spectrometer.

18. A method according to claim 17 wherein said inert carrier gases consist essentially of argon, and the concentrations of hydrogen, oxygen, and nitrogen in said molten metal are all determined by a single test procedure.

19. A method according to claim 13 wherein said second known concentration is zero.

20. A method according to claim 13 wherein a stream of pure inert carrier gas is introduced immediately after immersion of said probe for standardization and purging.

* * * * *